United States Patent [19]

Otey et al.

[11] 4,337,181
[45] Jun. 29, 1982

[54] BIODEGRADABLE STARCH-BASED BLOWN FILMS

[75] Inventors: Felix H. Otey; Richard P. Westhoff, both of Peoria, Ill.

[73] Assignee: The United States of America as represented by the Secretary of Agriculture, Washington, D.C.

[21] Appl. No.: 112,980

[22] Filed: Jan. 17, 1980

[51] Int. Cl.$^3$ ............................................. C08L 3/02
[52] U.S. Cl. ........................... 523/128; 260/DIG. 43; 524/47; 524/522; 524/556
[58] Field of Search ................ 260/17.4 ST, DIG. 43; 521/84, 149, 916

[56] References Cited

U.S. PATENT DOCUMENTS

| | | | |
|---|---|---|---|
| 2,676,929 | 4/1954 | Duddy | 521/84 |
| 3,274,731 | 9/1966 | Vigneault et al. | 260/DIG. 43 |
| 3,329,509 | 7/1967 | Julius | 260/17.4 ST |
| 3,488,724 | 1/1970 | Donermeyer et al. | 260/17.4 ST |
| 3,590,528 | 7/1971 | Shepherd | 260/45.85 |
| 3,952,347 | 4/1976 | Comerford et al. | 260/DIG. 43 |
| 4,016,117 | 4/1977 | Griffin | 260/DIG. 43 |
| 4,021,388 | 5/1977 | Griffin | 260/DIG. 43 |
| 4,026,849 | 5/1977 | Bagley et al. | 260/17.4 ST |
| 4,125,495 | 11/1978 | Griffin | 260/DIG. 43 |
| 4,133,784 | 1/1979 | Otey et al. | 260/17.4 ST |
| 4,138,453 | 2/1979 | Segl | 264/22 |
| 4,171,407 | 10/1979 | Elser | 260/17.4 ST |
| 4,207,221 | 6/1980 | Tobias et al. | 260/DIG. 43 |
| 4,218,350 | 8/1980 | Griffin | 260/17.4 ST |
| 4,228,047 | 10/1980 | Pippin | 260/17.4 ST |
| 4,251,584 | 2/1981 | Van Engelen et al. | 521/149 |

OTHER PUBLICATIONS

Chemical Abstracts 83, 115635s (1975).
Chemtech-Sep. 1973, pp. 552–562.
Chemtech-Sep. 1979, pp. 542–548.
Chemical Week 109 45, 49 (1971).
Chemical Week 110 44 (1972).

*Primary Examiner*—V. P. Hoke
*Attorney, Agent, or Firm*—M. Howard Silverstein; David G. McConnell; Curtis P. Ribando

[57] ABSTRACT

Film-forming formulations comprising starch, ethylene acrylic acid copolymer, and optionally polyethylene, can be blown into films upon neutralization of a portion of the copolymer acid functionality. The resultant biodegradable films have potential application as agricultural mulch, garbage bags, and various types of packaging.

10 Claims, No Drawings

BIODEGRADABLE STARCH-BASED BLOWN FILMS

BACKGROUND OF THE INVENTION

1. Field of the Invention

The United States produces more than 5 billion lbs. of plastic film each year, virtually all of which is made from petroleum-based raw materials. These films are most economically made by an economical extrusion blowing process in which a tubular extruded bubble is expanded and shaped by air streams at the die exit. In the field of agriculture, approximately 130 million lbs. of polyethylene (PE) film is used annually as mulch to improve crop yields by controlling weeds, retaining soil moisture, and reducing nutrient leaching. Since PE mulch cannot be reused and does not degrade between growing seasons, it must be removed from the field and disposed at a current estimated cost of $100 per acre. Other agricultural uses for plastic film include seedling containers and the protection of roots during transplanting. These films have also become an important factor in the packaging of consumer products and as containers for the disposal of waste.

Rapidly increasing prices, dwindling supplies of petroleum, and the need for economically feasible biodegradable films that do not adversely affect the environment upon disposal have intensified the need for alternate sources of raw materials for making plastics. This invention relates to the preparation of such films by the blowing of formulations based upon a renewable resource.

2. Description of the Prior Art

Numerous attempts have been made to produce degradable films from petroleum and cellulose-derived materials [Chemical Week 109: 45-46 (1971)] including PE-coated paper ]Chemical Week 110: 44 (1972)] and polybutene-1 films (U.S. Pat. No. 3,590,528). None has been completely successful, apparently because they were too costly, or they decompose too slowly for many applications. Starch is probably the most abundant, low-cost, biodegradable polymer available and its use in plastic film production would greatly reduce the demand for petrochemicals and the negative impact on the environment now caused by discarding nonbiodegradable films. Since starch alone forms a brittle film that is sensitive to water, it is generally understood that starch must be combined with other materials in order to produce a satisfactory product. PE is the most widely used material for producing films that have desirable physical properties for packaging and mulch applications, and it is available at a relatively low cost. It is therefore a particularly desirable material to combine with starch to achieve the desired flexibility, water resistance, and strength. However, previous attempts to produce blown films from compositions containing high levels of starch combined with PE have been unsuccessful.

Griffin (U.S. Pat. No. 4,016,117) teaches that about 8% predried starch (0.5% moisture), 90% PE, 1.6% ethyl oleate, and less than 1% oleic acid compositions can be converted to blown films (Example I). However, essentially the same composition could not be blown into a satisfactory film if the starch contained as much as 2% moisture (paragraph bridging columns 3 and 4; Example VII). The product became disfigured and weakened by the presence of numerous small bubbles created by the conversion of the free moisture to steam. This limitation on the moisture content requires special drying, handling, and storage techniques preparatory to film formation. Griffin further observed that both gelatinizing the starch (column 3, lines 36-39) and increasing the starch content of film formulations from 5 to 15% (Example XI) resulted in feel and crease retention properties much more paperlike than unmodified PE film.

The discovery by Otey et al. (U.S. Pat. No. 4,133,784) that compositions of ethylene arylic acid copolymer (EAA) and a starchy material can be formed into films that are flexible, water resistant, heat sealable, and biodegradable has intensified interest in the possibility of making starch-based films. These films were formed by either casting, simple extruding, or milling the starch-EAA composition. All are relatively slow processes that are considerably more expensive than the more conventional extrusion blowing technique. The relatively high processing cost coupled with the high price of EAA compared to PE tend to diminish this composition's potential for achieving large-scale commercial success. Also, at certain starch levels needed for achieving desired mechanical properties, the optimum degrees of biodegradability and UV stability are compromised.

Our attempts to incorporate pelletized PE into the pelletized EAA and starch composition described by Otey et al. (U.S. Pat. No. 4,133,734) and to convert the composite into blown films were not successful. Continuous blowing was difficult because the films ruptured. Visible striations and other evidence of poor compatibility between the starch and resin components were also indicative of an inferior product.

SUMMARY OF THE INVENTION

It has now been unexpectedly discovered that formulations containing up to about 60% gelatinized starch and various levels of EAA, and optionally PE, can be readily blown into high-quality biodegradable films having the feel and general appearance of conventional plastic films. These results are accomplished by the addition of a sufficient amount of neutralizing agent to neutralize part or all of the acidic portion of the EAA and by blowing the formulation at a moisture content in the range of about 2-10%. This discovery is entirely unexpected especially in view of Griffin's observations reported above. It was also a surprising discovery that when PE was incorporated into the composition, it increased both UV stability and biodegradability of the films.

In accordance with this discovery, it is an object of this invention to provide a method for blowing film-forming compositions at starch and moisture levels higher than heretofore possible.

It is also an object of the invention to prepare films that are stable to weathering conditions for a predetermined period and then decompose.

It is a further object of the invention to incorporate PE into starch-based films while maintaining or enhancing their biodegradability.

Other objectives and advantages of the invention will become readily apparent from the ensuing disclosure.

DETAILED DESCRIPTION OF THE INVENTION

"Films," such as those made in accordance with the invention, are defined by the polymer industry (Encyclopedia of Polymer Science and Technology, John Wiley and Sons, Inc., 1967, Vol. 6, page 764) as "shaped plastics that are comparatively thin in relation to their breadth and width and have a maximum thickness of 0.010 in." Self-supporting films are those "capable of supporting their own weight." "Uniform films" as used in this application refer to those which are virtually free of breaks, tears, holes, bubbles, and striations.

"Composite" is defined herein in accordance with The American Heritage Dictionary of the English Language, New College Edition, published by Houghton Mifflin Company, page 273, to mean "a complex material . . . in which two or more distinct, structurally complementary substances, especially . . . polymers, combine to produce some structural or functional properties not present in any individual component."

The term "extrusion blowing" is well known in the art and distinguishes from simple extrusion in that it relates to shaping a tubular extrudate, or "bubble" into its final form by internal and external cooling streams of air, the internal stream causing expansion of the bubble to several times the size of the die opening. Films prepared by this technique are commonly referred to as "blown films."

The starch-based films of the invention are prepared from any unmodified starch from cereal grains or root crops such as corn, wheat, rice, potato, and tapioca. The amylose and amylopectin components of starch as well as modified starch products such as partially depolymerized starches and derivatized starches may also be used. The term "starchy materials" as used in the specification and in the claims is defined herein to include all starches, starch flours, starch components, and modified starch products as described above.

In the preparation of the instant starch-based films, the starchy materials must be partially or completely gelatinized. Gelatinization is effected by any known procedure such as heating in the presence of water or an aqueous solution at temperatures of about about 60° C. until the starch granules are suffiently swollen and disrupted that they form a smooth viscous dispersion in the water. The gelatinization may be carried out either before or after admixing the starchy material with the EAA as discussed further below.

The EAA copolymer must have sufficient carboxyl functionality so as to be compatible with the starch for purposes of preparing the disclosed films. It is believed that the pendant carboxyl groups supplied by the acrylic acid component associate with the hydroxyl groups of the starch, thereby contributing to the compatibility and composite formation of the starch and the EAA. These carboxyl groups coincidentally contribute to the water dispersibility of the copolymer. We have found as a rule of thumb that if the EAA is water dispersible, it will also be sufficiently compatible with the starch.

The preferred EAA is a water-dispersible product prepared by copolymerizing a mixture comprising about 20% acrylic acid and 80% ethylene, by weight. However, it is to be understood that EAA copolymers having somewhat different proportions of polymerized acrylic acid and ethylene would also yield acceptable starch-based films provided that they contain a sufficient number of carboxyl groups to be water dispersible.

The preferred neutralizing agent for use in the invention is ammonia in either its anhydrous or aqueous form. The amount added to the film compositions may be varied over a wide range so long as enough is initially present to equal at least about one-half equivalent per equivalent of acid in the EAA. Normally the level of ammonia addition will be about 0.8-5 weight percent based on the dry weight of the starch-EAA-PE formulation. The ammonia is believed to form an ammonium salt with the acid as evidenced by an infrared spectrophotometer peak in the range of a carbonyl salt observed in the final film product. Any excess ammonia added to the formulation tends to be driven off during the processing steps described below. Likewise, it is expected that a portion of the ammonia associated with the EAA volatilizes during blowing. Other suitable neutralizing agents would include simple amines which are substantially similar to ammonia in their tendency to form salts with organic acids.

The moisture content of the film formulation just prior to and after blowing must be maintained within the range of about 2 to 10% (w/w) and preferably between 5 and 8%. Compositions with moisture contents outside of this range do not produce a uniform, continuous film. If the starch has been pregelatinized, its moisture content at the time of addition is not particularly critical provided that enough moisture is available in the system to permit dispersing the EAA. If the added starch is granular, sufficient moisture must be provided to allow partial or complete gelatinization. Either way, during the initial mixing of the formulation components, at least 10% and preferably 20 to 50% by weight moisture, based on total solids, should be present, Excess moisture is then removed from the composition by evaporation during the processing operations.

While the inclusion of PE in the film formulation is desirable from an economic standpoint, it suprisingly increases the UV stability and the rate of biodegradation of the resulting products. Any grade of PE that can be blown into a film is suitable for the instant process. Low density PE is normally used for this purpose.

The proportions of starchy material, EAA, and PE may be varied over wide ranges in order to tailor the resultant film properties to the desired end use. Based upon the combined weight of these three components, the starchy material content may be in the range of 10-60%, and preferably on the order of 30-40%. As the starch level approaches 60%, the weather and tear resistance drop considerably, the film becomes translucent, and the other physical properties become fair to poor. Acceptable levels of EAA copolymer are in the range of 10-90%, with the preferred amount being in the range of about 30-70%, depending on the proportion of PE. PE levels may range from 0-80%, but at a starch content of 30-40%, PE amounts in the range of 10-40% are preferred for acceptable physical properties and blowing characteristics.

If the starch is to be gelatinized during the mixing operation, the formulation should be heated to at least 60° C. Simultaneous gelatinization and EAA melting are preferably conducted at temperatures of 95°-100° C. The gelatinized starch and melted EAA form a homogeneous plasticized matrix. In the second stage of heating and mixing, temperatures of 125°-145° C. are suitable for adjusting the moisture content to the appropriate range for blowing, and for fluxing any added PE into the matrix. Since the formulations are readily blown at these temperatures, further temperature adjustment is unnecessary. Of course, the gelatinization, mixing, moisture reduction, and film blowing could all be conducted in one continuous operation using commercial equipment with heating, mixing, venting, and extrusion blowing capability.

While the ammonia may be added at almost any time prior to blowing, it is most advantageously incorporated toward the end of the heating operation in order to minimize losses by evaporation. Immediately upon addition of the ammonia, the viscosity of the matrix increases rapidly, suggesting a significant change in the composition due to its presence.

The blown film product is a flexible composite of the gelatinized starch, the EAA ammonium salt, and the PE (if present). Without desiring to be bound to any particular theory, it is believed that the EAA salt associates with the gelatinized starch molecules and holds them in the same expanded flexible state in which they exist in the heated matrix.

Other materials, either polymeric or monomeric, may be added to the composition in order to achieve specific properties in the film. For example, polyvinyl alcohol may be added in varying amounts to improve the rate of biodegradation, and UV stabilizers such as carbon black can be added to greatly improve resistance of the film to sunlight. Other additives include those conventionally incorporated into agricultural mulches and packaging films including fungicides, herbicides, antioxidants, fertilizers, opacifying agents, stabilizers, etc. These materials and additives may be employed in conventional amounts as determined by the skilled artisan, and may collectively comprise up to 80% of the film composition.

By continuous feeding of the plasticized formulations of this invention into the blowing apparatus, continuous blown films can be readily obtained. It is also obvious to those skilled in the art that these formulations could be extruded into thin film, rods, or hollow tubing or that they could be injection-molded into finished products that would be biodegradable.

The following examples further illustrate the invention but should not be construed as limited the invention which is defined by the claims.

All percents herein disclosed are "by weight" unless otherwise specified.

EXAMPLES 1–5

Blown Film Preparations: Starch-EAA.

A mixture of air-dried corn starch (11% moisture) and enough water to equal the total solids in the final composition were blended for 2–5 min.. at 95° C. in a steam-heated Readco mixer (type: 1 qt. Lab. made by Read Standard Div., Capitol Products Corp., York, PA) to initiate gelatinization of the starch. EAA pellets (type: 2375.33 manufactured by Dow Chemical Co.) were added, and heating at 95° C. to 100° C. and mixing were continued for about 45 min. during which time the EAA melted and the formulation was converted into a uniform matrix. Aqueous ammonia was then added and the viscosity of the matrix rapidly increased. Mixing was continued for about 5 min. Due to water loss by evaporation, the resultant matrix contained about 25 to 35% moisture. To further reduce the moisture content, the matrix was extrusion processed with an extrusion head attached to a Brabender Plasti-Corder (type: PL-V300 manufactured by C. W. Brabender Instruments, Inc., South Hackensack, N.J.). The screw of the extruder was ¾-in. in diameter, 9 in. long, and had a compression ratio of 2:1. The die consisted of 24 circular holes of 1/32-in. diameter. This extrusion process was repeated usually one or two more times until the moisture content of the exudate was between about 5 to 10%. The exudate was a transparent, flexible, strong plastic. This material was blown into a film by passing it through the same extruder except that the die was replaced with a heated ½-in. blown film die. The screw r.p.m. was about 70–80, torque reading was 400–500 meter-grams, barrel temperature was 120°–130° C., and the die temperature was set in the range of 125°–145° C.

Compositions and properties of films prepared by this procedure are reported in the Table, below. The physical properties were determined by standard procedures. Tensile strength was measured on a "Scott Tester" and is reported as the maximum load per unit area of original cross-section required to break a test specimen. The percent elongation is the extension recorded when the specimen ruptured, expressed as a percentage of the original length of the section under test. The "Weather-Ometer" data indicates the number of hours until the sample showed cracks in a twin arc model DMC-HR Weather-Ometer (Atlas Electric Devices Co.) operated on a cycle of 120 min. of light only followed by 18 min. of light and water spray using a black panel temperature of 63° C.

EXAMPLES 6–10

Blown Film Preparations: Starch-EAA-PE.

The procedure of Examples 1–5 was repeated except that PE pellets were added to the formulation about 15 min. after EAA addition. Since the temperature conditions of the Readco mixer were insufficient to melt the pellets, the extrusion through the 24-hole die was preceded by two or three extrusions through a ¼-in. orifice at a barrel temperature of about 135° C. to flux the PE. During the extrusion blowing operation, higher levels of PE required temperatures near the upper end of the 125°–145° C. range.

Compositions and properties of films prepared by this procedure are reported in the Table. The MIT fold test conducted with a "Folding Endurance Tester" (Tinius Olson Testing Machine Co.) shows the number of times a specimen can be folded before breaking when subjected to continuous folding through an angle of 135° under a tension of 500 g. The burst factor data was collected with a "Mullen Tester" (B. F. Perkins and Son, Inc.) and indicates the amount of pressure required to rupture a specimen.

TABLE

| Example No. | Formulation, %[a,b] | | | Tensile strength, p.s.i. | Elongation, % | Ammonia[c] | MIT fold, No. folds | Burst factor | "Weather-Ometer," hours | Fungi susceptibility, weeks[d] | | | |
|---|---|---|---|---|---|---|---|---|---|---|---|---|---|
| | Starch | EAA | PE | | | | | | | 1 | 2 | 3 | 4 |
| 1 | 10 | 90 | 0 | 3470 | 260 | 4.9 | — | — | 402 | 0 | 0 | 0 | 0 |
| 2 | 20 | 80 | 0 | 4140 | 120 | 4.3 | — | — | 212 | 0 | 0 | 0 | 0 |
| 3 | 30 | 70 | 0 | 3225 | 150 | 3.8 | — | — | 168 | 0 | 0 | 0 | 0 |
| 4 | 40 | 60 | 0 | 3870 | 92 | 3.3 | — | — | 90 | 1— | 1 | 1 | 1 |
| 5 | 50 | 50 | 0 | 3940 | 61 | 2.7 | — | — | 90 | 1+ | 2+ | 3 | 3+ |
| 6 | 40 | 50 | 10 | 3570 | 80 | 3.6 | 3800 | 24 | 111 | 2 | 3 | 4 | 4 |
| 7 | 40 | 40 | 20 | 3477 | 66 | 2.2 | 7000 | 24 | 134 | 1 | 2 | 3 | 4 |

TABLE-continued

| Example No. | Formulation, %[a,b] | | | Tensile strength, p.s.i. | Elongation, % | Ammonia[c] | MIT fold, No. folds | Burst factor | "Weather-Ometer," hours | Fungi susceptibility, weeks[d] | | | |
| --- | --- | --- | --- | --- | --- | --- | --- | --- | --- | --- | --- | --- | --- |
| | Starch | EAA | PE | | | | | | | 1 | 2 | 3 | 4 |
| 8 | 40 | 30 | 30 | 3150 | 36 | 1.7 | 2700 | 21 | 134 | 1 | 2 | 3 | 4 |
| 9 | 40 | 20 | 40 | 2920 | 34 | 2.8 | 4800 | 19 | 199 | — | — | — | 4 |
| 10 | 40 | 10 | 50 | 1840 | 10 | 2.8 | 470 | 9 | 559 | — | — | — | 4 |

[a]Based on combined dry weight of starch, EAA, and PE, exclusive of water and $NH_3$.
[b]Formulations of Examples 4, 6, 9, and 10 additionally contained about 1% antioxidant ("Irganox 1035," Ciba Geigy Corp.).
[c]Parts of ammonia per 100 parts of formulation dry weight.
[d]ASTM D 1924-70. Larger numbers indicate more fungal attack.

Blown Film Properties

Properties of film samples from Examples 1–5 reveal effects of increasing the starch level from 10% to 50% without any PE in the formulation. All of the films containing up to 50% starch were transparent, flexible, self-supporting, and generally were considered to have good physical properties. However, the degree of transparency and flexibility decreased slightly as the level of starch was increased. All of the samples were uniform and indicated that good compatibility existed between the starch and EAA. It was apparent from the general appearance of these films, their blowing rate, and the flow characteristics of their plasticized formulations that the maximum level of starch which could be incorporated to achieve acceptable films was about 60%, with the preferred level at about 40%. As the starch level increased, there was a significant decrease in film resistance to artificial weathering in a "Weather-Ometer." Deterioration was attributed to UV instability which caused small cracks or tears in the film. More significantly was the lack of fungal attack under controlled conditions with up to 30% starch and a very slow attack with 40% starch present. While it is expected that all the films are biodegradable, the ASTM method used for measuring fungal attack did not extend beyond 4 wks.

Examples 6–10 reveal that films with 40% starch and up to about 40% PE were clear, flexible, self-supporting, and uniform, indicating good compatibility. Above about 40% levels of PE, the films were less transparent and in some instances translucent, and were observed to have less tear resistance. In contrast, to the film samples without PE, the films prepared in Examples 6–10 reflect a substantial increase in resistance to "Weather-Ometer" exposure as increasing amounts of PE were incorporated into formulations. Furthermore, the addition of PE greatly increased the fungal attack on the samples showing that the film would biodegrade more readily when exposed to outdoor soil contact.

Films corresponding to those prepared in Examples 4 and 8 were subjected to a 35-da. outdoor exposure test. The film with 40% starch and 60% EAA developed cracks within 11–13 da. while that containing 40% starch, 30% EAA, and 30% PE did not develop any cracks.

EXAMPLE 11

Starch-EAA: The Effects of Ammonia Omission and Vapor Treatments

A composition was prepared essentially as described in Examples 1–5 except that ammonia was omitted from the formula. Exclusive of moisture, the formulation contained 40% starch, 59.5% EAA, and 0.5% pentachlorophenol (fungicide). After the mixing and extruding through the 24-hole die, the matrix was blended cold on a rubber mill for 2–3 min. One-half of this product was passed through the blown film die. The film contained streaks indicating poor compatibility. The blown film was then exposed to ammonia vapors in a closed container for a few minutes and again passed through the blown film die to produce a clear, uniform film with good physical properties.

The remaining half of the rubber-milled products was sealed in a plastic bag containing aqueous ammonia for a few minutes and then passed through the blown film die to produce a good quality, uniform, clear film.

EXAMPLE 12

Starch-EAA-PE: The Effect of Ammonia Omission

A composition was prepared as described in Examples 6–10 except that ammonia was omitted from the formula. Exclusive of moisture, the formulation contained 40% starch, 30% EAA, and 30% PE. The matrix was repeatedly passed through the blown film die but a clear, uniform film could not be obtained. The film contained white spots and frequently ruptured during the blowing attempts.

EXAMPLE 13

Composition Containing Carbon as a UV Stabilizer

A composition was prepared as described in Examples 6–10 except that carbon black (Industrial Reference black No. 3) was blended into melted EAA prior to blending the other components. Composition of the blown film, exclusive of moisture and ammonia, was 5% carbon black, 32.5% EAA, 32.5% PE, and 30% starch. The blown film had a tensile strength of 2000 p.s.i., elongation of 62%, and withstood "Weather-Ometer" exposure for 710 hr. before any cracks or evidence of deterioration occurred.

EXAMPLE 14

Composition Containing Polyvinyl Alcohol, Sorbitol, and Glycerol

A mixture of air-dried corn starch (11% moisture) polyvinyl alcohol (Vinol 425 made by Air Products and Chemicals, Calvert City, KY), sorbitol, glycerol, and enough water to equal the weight of total solids in the formula was blended at 95° C. in the Readco mixer for 1 1/6 hr. Then enough aqueous ammonia was added to equal about 2.6% ammonia based on the dry solids weight of the composition. After another ⅓ hr. of mixing, the composition was passed twice through the 24-hole extrusion head and then the blown film die as described in Examples 1–10. A transparent flexible film was obtained that had a tensile strength of 3500 p.s.i. and an elongation of 300%. The dry film composition was 25% starch, 25% PVA, 18% sorbitol, 2% glycerol, and 30% EAA. When exposed to soil microorganisms according to ASTM D 1924-70, 100% of the sample was covered with mold growth within 1 wk.

EXAMPLE 15

A film was prepared essentially as described in Examples 6-10, except the composition of the final dry film was 30% starch, 10% polyvinyl alcohol, 30% EAA, and 30% PE. Tensile strength of the film was 2096 p.s.i., elongation was 25.5%, the fungi susceptibility was 4 after 4 wk. as described by ASTM D 1924-70, and the blown film was resistant to "Weather-Ometer" conditions for 146 hr.

EXAMPLE 16

In the Brabender mixer was melted a quantity of EAA pellets. The air-dried starch (12.2% moisture) was slowly added with mixing to the molten EAA at about 90° C. and the formulation stirred for 15 min. to form a matrix. Aqueous ammonia was added to the matrix and stirring was continued for another ¼ hr. The product was then blown into a film using the same ½-in. blown film die and procedure as described in Examples 1-5. Composition of the film exclusive of moisture and ammonia was 40% starch and 60% EAA. The amount of ammonia added was equal to 3.5 parts per hundred parts of starch plus EAA. The blown film had a tensile strength of 2404 p.s.i. and an elongation of 82%.

We claim:

1. In a method of producing a flexible, self-supporting, and biodegradable film wherein a mixture comprising a partially or completely gelatinized starchy material in an amount up to 60% by weight and an ethylene acrylic acid copolymer is converted into a plasticized matrix and then shaped into said film, the improvement comprising the following steps:
   a. incorporating into said matrix a neutralizing agent selected from the group of aqueous ammonia and anhydrous ammonia;
   b. adjusting the moisture content of said matrix to within the range of about 2-10% based on the weight of the matrix; and
   c. extrusion blowing said ammoniated and moisture-adjusted matrix into a film.

2. The method as described in claim 1 and further comprising incorporating polyethylene into said matrix.

3. A flexible, self-supporting, a biodegradable film composition prepared by the process of claim 2.

4. A composition as described in claim 3 wherein the amount of starchy material is in the range of 10-60%, the amount of ethylene acrylic acid copolymer salt expressed in terms of its acid form is the range of 10-90%, and the amount of polyethylene is in the range of 10-80%, all based upon the combined dry weight of the starchy material, the ethylene acrylic acid copolymer, and the polyethylene.

5. The method as described in claim 1 wherein said neutralizing agent is incorporated into said matrix prior to adjusting the moisture content to within the range of step (b).

6. The method as described in claim 1 wherein said neutralizing agent is incorporated into said matrix subsequent to adjusting the moisture content to within the range of step (b).

7. The method as described in claim 1 wherein said mixture comprises an amount of starchy material in the range of about 10-60%, an amount of ethylene acrylic acid copolymer in the range of about 10-90%, and an amount of polyethylene in the range of about 0-80%, all based upon their combined dry weight.

8. A flexible, self-supporting, and biodegradable film composition prepared by the process of claim 1.

9. A composition as described in claim 8 wherein said starchy material is selected from the group consisting of unmodified starches and flour.

10. A composition as described in claim 8 wherein said starchy material is an unmodified starch selected from the group consisting of cereal grain starches and root crop starches.

* * * * *